US012274800B2

(12) United States Patent
Chai et al.

(10) Patent No.: US 12,274,800 B2
(45) Date of Patent: Apr. 15, 2025

(54) TUBE STERILIZATION SYSTEM USING AN LED UV EMITTER

(71) Applicant: LUMILEDS LLC, San Jose, CA (US)

(72) Inventors: Yan Chai, San Jose, CA (US); Franklin Chiang, Campbell, CA (US)

(73) Assignee: Lumileds LLC, San Jose, CA (US)

( * ) Notice: Subject to any disclaimer, the term of this patent is extended or adjusted under 35 U.S.C. 154(b) by 713 days.

(21) Appl. No.: 17/506,187

(22) Filed: Oct. 20, 2021

(65) Prior Publication Data

US 2022/0118139 A1 Apr. 21, 2022

Related U.S. Application Data

(60) Provisional application No. 63/094,475, filed on Oct. 21, 2020.

(51) Int. Cl.
*A61L 2/10* (2006.01)
*A61L 2/26* (2006.01)

(52) U.S. Cl.
CPC ................................ *A61L 2/10* (2013.01); *A61L 2/26* (2013.01); *A61L 2202/14* (2013.01); *A61L 2202/24* (2013.01)

(58) Field of Classification Search
CPC ........................................................ A61L 2/10
See application file for complete search history.

(56) References Cited

U.S. PATENT DOCUMENTS

| 9,492,574 | B2 | 11/2016 | Rasooly et al. | |
| 2006/0167531 | A1* | 7/2006 | Gertner | A61N 5/0603 607/86 |
| 2008/0159908 | A1 | 7/2008 | Redmond | |
| 2008/0257355 | A1* | 10/2008 | Rao | A61L 2/16 128/207.14 |
| 2011/0213339 | A1 | 9/2011 | Bak | |
| 2013/0323119 | A1* | 12/2013 | Alwan | A61L 2/10 250/455.11 |
| 2016/0038621 | A1* | 2/2016 | Victor | A61M 25/0017 128/202.16 |
| 2017/0174536 | A1 | 6/2017 | Robison et al. | |

* cited by examiner

*Primary Examiner* — Kevin Joyner

(57) ABSTRACT

The invention generally relates to a catheter sterilization system using semiconductor light emitting devices (LEDs) to sterilize the lumen of a catheter. The sterilization system may include a sterilization head with attached semiconductor LEDs sized for insertion into the catheter. The sterilization head is connected to the linearly extending connector allowing an operator to move the sterilization head through the catheter. The sterilization system may alternatively include microLEDs attached to the inner sidewalls of the catheter to sterilize the lumen of the catheter.

10 Claims, 8 Drawing Sheets

TUBE STERILIZATION SYSTEM USING AN LED UV EMITTER

CROSS REFERENCE TO RELATED APPLICATIONS

This application claims benefit of priority to U.S. Provisional Patent Application No. 63/094,475 filed Oct. 21, 2020, which is incorporated herein by reference in its entirety.

TECHNICAL FIELD

The present disclosure generally relates to a catheter sterilization or germicidal system that uses ultraviolet or near ultraviolet radiation to sterilize the lumen of the catheter.

BACKGROUND

Semiconductor light-emitting devices (LEDs) can be manufactured to emit high intensity ultraviolet germicidal radiation. Ultraviolet germicidal irradiation (UVGI) is a disinfection method that uses short-wavelength ultraviolet (UV-c) light to kill or inactivate microorganisms by destroying nucleic acids and disrupting their DNA, leaving them unable to perform vital cellular functions. UVGI is used in a variety of applications, such as food, air, and water purification. The application of UVGI to disinfection has been an accepted practice since the mid-20th century. While it has long been used in medical sanitation and sterile work facilities, UV radiation has increasingly been employed to prevent build-up of bacteria (e.g., *Pseudomonas aeruginosa, Staphylococcus aureus, Escherichia coli*, etc.) that could pose a danger to patients.

Current UVGI systems are designed to expose surfaces such as counter tops, surgical tools, and personal protective equipment to germicidal UV. Exposure comes from germicidal lamps that emit germicidal UV at the correct wavelength, thus irradiating the environment. These systems generally use mercury-based lamps operating at low vapor pressure, pulsed-xenon lamps, or more recently, ultraviolet light-emitting diodes (UV-C LED) that emit light at wavelengths between 230 nm and 280 nm. Because the emitting area of these systems are large, they are generally not used to sterilize the interior of medical devices inside patients, such as catheters, without proper coupling of the light (e.g., through fiber optic cables) and blocking the light from damaging the patient's body. Medical devices such as catheters are essentially long, thin, flexible tubes used to deliver air, medicines, fluids, nutrients, or blood products over a long period of time to a patient. However, due to the sustained presence of these devices in a patient, catheters are at risk of becoming contaminated with dangerous bacteria or viruses in a manner that can cause dangerous secondary infections to the patients. Generally, a catheter must be changed periodically due to this risk of contamination. But removing and inserting a new catheter is a painful process for the patient. There exists a need for better ways to sterilize a catheter.

SUMMARY

In one embodiment, a sterilization system includes a UV radiation sterilization system including a linearly extending connector sized for insertion into a tube having inner sidewalls. A sterilization head is connected to the linearly extending connector, with at least one semiconductor LED emitter of UV radiation arranged to direct UV radiation toward the inner sidewalls and positioned between forward and rear UV blocking caps.

In some embodiments the linearly extending connector is flexible.

In some embodiments the linearly extending connector further provides an electrical connection to at least one semiconductor LED emitter.

In some embodiments a battery power module is connected to the sterilization head.

In some embodiments at least one optic is positioned to receive light from at least one semiconductor LED emitter.

In some embodiments at least one of a UV reflector or absorber is attached to the sterilization head.

In one embodiment, a sterilization head includes a housing connectable to the linearly extending connector. The housing has forward and rear UV blocking caps and at least one semiconductor LED emitter of UV radiation arranged to direct UV radiation outward and positioned between the forward and rear UV blocking caps.

In one embodiment, semiconductor microLED emitters are attached to the inner wall of a catheter to sterilize the lumen of catheter. This embodiment provides a sterilization system with few moving parts and greater convenience and ease in the sterilization process.

BRIEF DESCRIPTION OF THE DRAWINGS

Non-limiting and non-exhaustive embodiments of the present disclosure are described with reference to the following figures, wherein like reference numerals refer to like parts throughout the various figures unless otherwise specified.

DETAILED DESCRIPTION

Figure 1:
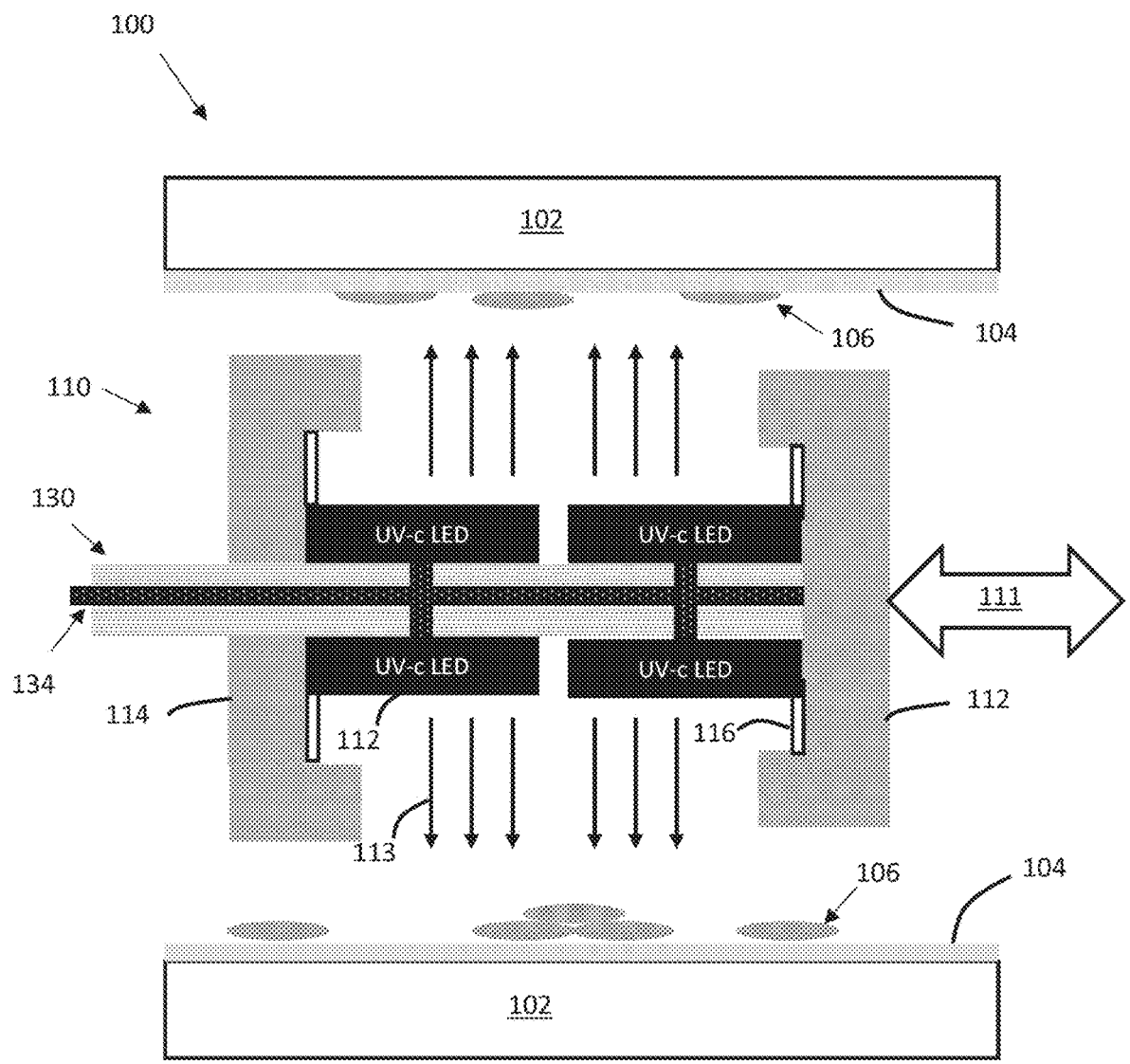
FIG. 1 is an illustration of a UV sterilization system for tube interiors, channels, or other confined spaces.

FIG. 1 illustrates an example embodiment of a UV sterilization system. The UV sterilization system 100 can sterilize tubing 102, or alternatively, channels or constrained areas difficult to reach with traditional cleaning tools. The tubing 102 may be a catheter, i.e., a tubular medical device for insertion into body cavities, canals, vessels, or passageways. Examples of catheters include, but are not limited to, endotracheal tubes and central venous catheters. FIG. 1 shows a cross section of tubing 102 along the length of the tubing, i.e., along the long axis of the tubing. The tubing 102 can be contaminated with bacteria, viruses, protozoa, other organisms, or toxins (represented by not to scale organisms 106) that can be inactivated by UV light. To improve safety, the sidewalls of tubing 102 can incorporate UV absorbers, and/or the tubing sidewalls can be lined with a UV reflecting material 104 (e.g., silver). The UV absorbers and/or UV reflective lining 104 protects patient tissue from UV light exposure during the catheter disinfection procedure.

The UV sterilization system 100 can further include a sterilization head 110 that includes a housing connected to the linearly extending connector 130. The linearly extending connector 130 extends in the lengthwise direction into the lumen of tubing 102. The linearly extending connector 130 can be a rigid, semi-rigid, or flexible structure formed as a solid or hollow cable or wire. Materials used can be sterilizable. In some embodiments, electrical wires, power cables, electrical strips, control or data signal cables 134 can be run through the connector 130 to extend into the sterilization head 110. In operation, pushing or pulling the linearly extending connector 130 can cause movement 111 back and forth in the lengthwise direction through the tube 102. In the embodiment of FIG. 1, the linearly extending connector 130 is connected to sterilization head 110 at a central axis of the sterilization head.

The housing of the sterilization head 110 has at least one semiconductor LED emitter 112 of UV radiation 113 arranged to direct UV radiation 113 outward from the housing of the sterilization head 110 toward the sidewalls of tubing 102. The LED emitter 112 is arranged so that the light emission surface of the LED is substantially parallel to the long axis of tubing 102. This arrangement substantially restricts the LED emitter to sterilizing the immediately adjacent sidewall surfaces of tubing 102. This advantageously allows the operator to better control which sections of tubing 102 receives UV radiation and minimizes UV radiation exposure to the patient. The UV radiation 113 is preferably UV-C radiation with wavelengths of between 230 nm and 280 nm. The semiconductor LED emitter 112 can be positioned between forward 112 and rear 114 UV blocking caps. In some embodiments the forward 112 and rear 114 UV blocking caps provide complete or partial UV blocking. In some embodiments, the forward 112 and rear 114 UV blocking caps extend above the light emitting surface of LED emitter 112 to completely or partial block UV radiation 113 from traveling in a lengthwise direction through tubing 102. Alternatively, or in addition, UV reflectors 116 or absorbers can be attached or applied to inner or outer walls of the UV blocking caps of the sterilization head 110 to block UV radiation from traveling in a lengthwise direction through tubing 102. In some embodiments, a window or gap in UV absorbent or reflective housing materials of the sterilization head can be made to allow UV to be directed at the tubing 102. To improve efficiency, UV reflectors 116 can be attached to all or part of the sterilization head 110 to redirect light out toward the sidewalls of tubing 102.

In some embodiments the one or more LED UV emitters 112 can be constructed from patterned or unpatterned sapphire, silicon, or silicon carbide that is able to support epitaxially grown or deposited semiconductor LED layers. In one embodiment, a semiconductor p-layer can be sequentially grown or deposited on an n-layer, forming an active region at the junction between layers. Semiconductor materials capable of forming high-brightness light emitting devices can include, but are not limited to, Group III-V semiconductors, particularly binary, ternary, and quaternary alloys of gallium, aluminum, indium, and nitrogen, also referred to as III-nitride materials. UV wavelength emitted can range from 230 nm to 310 nm, with narrower ranges possible. In some embodiments, several LED UV emitters having differing UV wavelength emission characteristics can be used. Advantageously, use of multiple UV wavelengths can allow better targeting of, for example, bacterial versus viral microorganisms.

The LED UV emitters 112 can be packaged and hermetically sealed against fluid using UV tolerant materials such as spin on glass. In some embodiments, the LED UV emitters 112 are attached to a rigid, semi-rigid, or flexible submount or printed circuit board that is connected to or formed as part of the linearly extending connector 130. The LED UV emitters 112 can be connected for powering and controlling UV emission by the semiconductor LEDs 112. In certain embodiments, the printed circuit board can also include electrical vias, heat sinks, ground planes, electrical traces, and flip chip or other mounting systems. The submount or printed circuit board may be formed of any suitable material, such as ceramic, silicon, aluminum, etc. If the submount material is conductive, an insulating layer is formed over the substrate material, and the metal electrode pattern is formed over the insulating layer. The submount acts as a mechanical support, provides an electrical interface between electrodes on the LED and a power supply, and provides heat sinking.

The LED UV emitters 112 can be microLEDs. LEDs having dimensions in the plane of the light emission surface of the LED (e.g., side length) of less than or equal to about 50 microns are typically referred to as microLEDs. The LED UV emitters 112 can be a microLED array which comprises an array of microLEDs. A microLED array can comprise a three-by-three array of nine microLEDs, although such microLED arrays may include for example tens, hundreds, or thousands of individual microLEDs. MicroLEDs in such an array may be spaced apart from each other by streets or lanes having a width in the plane of the array of, for example, less than or equal to 50 microns, less than or equal to 10 microns, or less than or equal to 5 microns. An array of microLEDs, or portions of such an array, may be formed as a segmented monolithic structure in which individual microLEDs are electrically isolated from each other by trenches and/or insulating material, but the electrically isolated segments remain physically connected to each other by portions of the semiconductor structure. The individual microLEDs in a microLED array may be individually addressable, may be addressable as part of a group or subset of the microLEDs in the array, or may not be addressable. Thus, microLED arrays are useful for any application requiring or benefiting from fine-grained intensity, spatial, and temporal control of light distribution. The emitted light may be spectrally distinct, adaptive over time, and/or environmentally responsive. Such microLED arrays may provide pre-programmed light distribution in various intensity, spatial, or temporal patterns. In operation, illumination from some or all microLEDs of the array may be adjusted—deactivated, operated at full intensity, or operated at an intermediate intensity. Beam focus or steering of light emitted by the microLED array can be performed electronically by activating one or more subsets of the pixels, to permit dynamic adjustment of the beam shape.

In still other embodiments primary or secondary optics can be attached to or positioned near LED UV emitters 112. Optics can include collimators, wave guides, concave or convex lenses, lenslet arrays, graded index lens, reflectors, scattering elements, beam homogenizers, diffusers, or other light focusing or blurring optics. Protective layers, transparent layers, thermal layers, or other packaging structures can be used as needed for specific applications.

Figure 2:
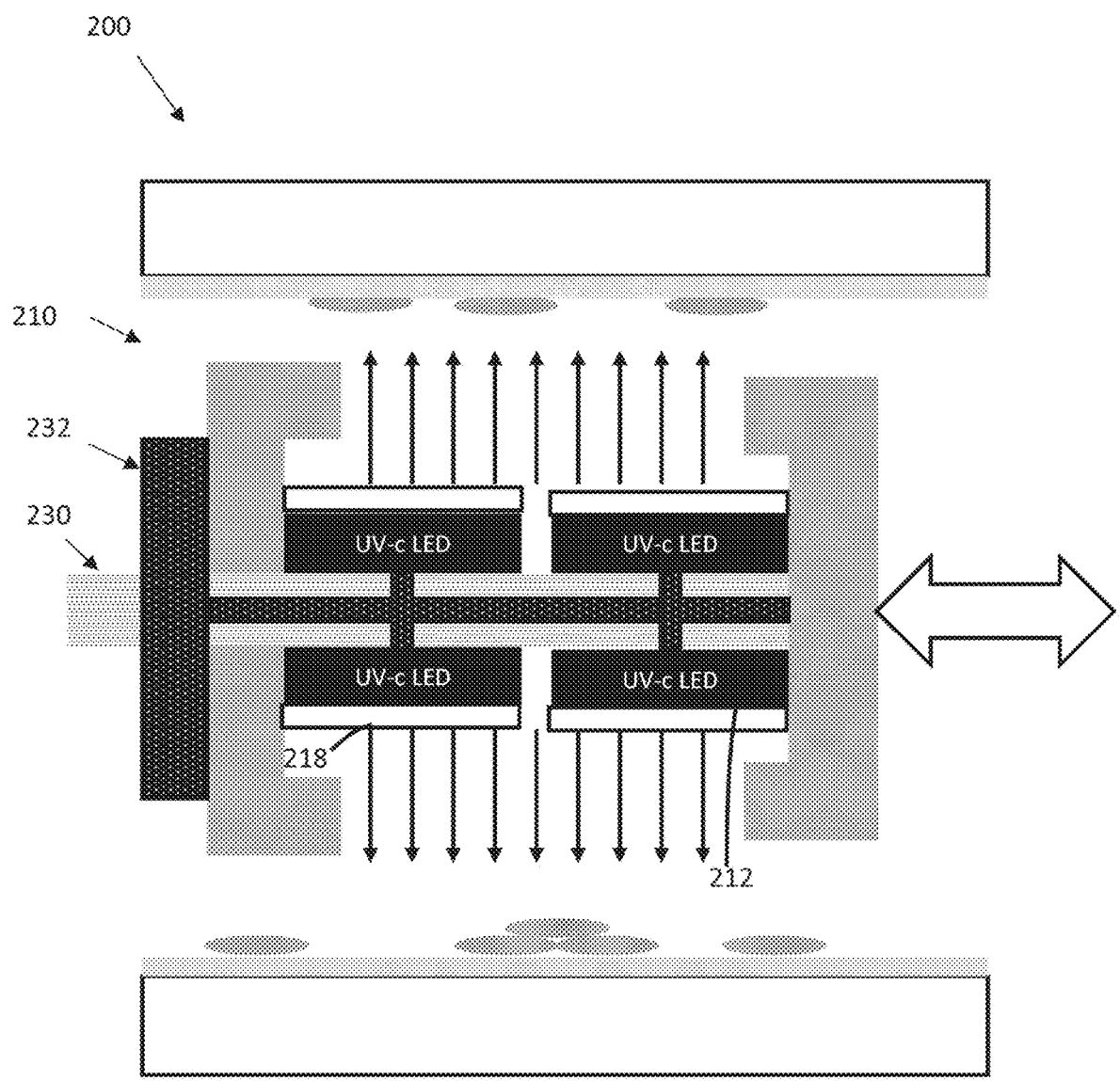
FIG. 2 is an illustration of an alternative UV sterilization system with a built-in battery.

FIG. 2 is an illustration of an alternative embodiment of a UV sterilization system 200 similar to that described with respect to FIG. 1. In this embodiment, a sterilization head 210 is attached to a power and control system 232. Further, a linearly extending connector 230 can be used to move the sterilization head 210 back and forth in the lengthwise direction through contaminated tubing or catheter. In some embodiments, the linearly extending connector 230 does not need to support electrical power lines, since LED UV emitters 212 can be powered by batteries or other local power sources in the power and control system 232. Additionally, the sterilization head 210 can include optics 218 attached to direct or focus UV light from the LED UV emitters 212.

Figure 3:
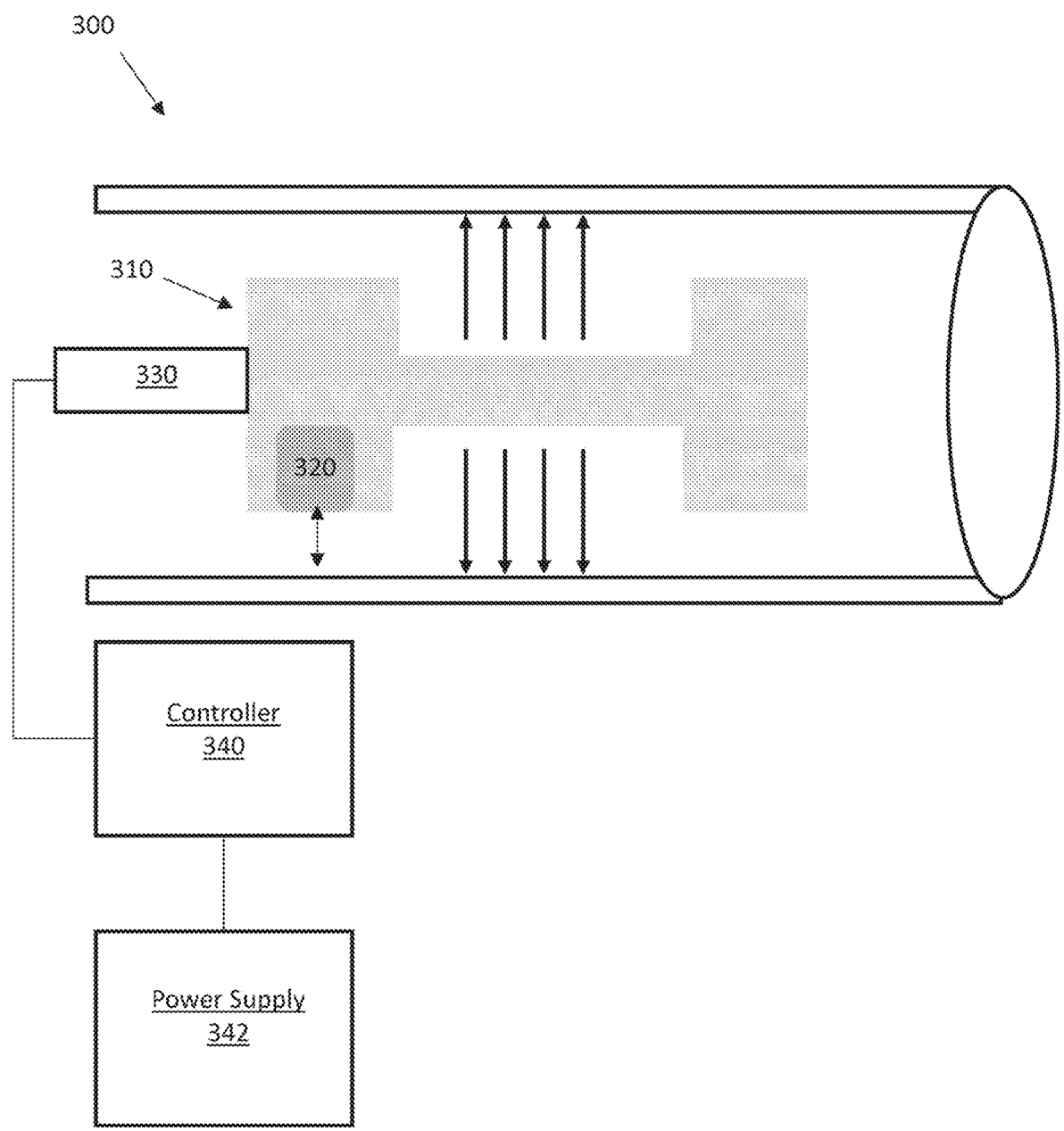
FIG. 3 is an illustration of an alternative UV sterilization system having sensors connected to a controller and power supply.

FIG. 3 is an illustration of an alternative embodiment of a UV sterilization system 300 similar to that described with respect to FIGS. 1 and 2. In this embodiment, a sterilization head 310 is attached to a controller 340 and power supply 342. Further, a linearly extending connector 330 can be used to move the sterilization head 310 back and forth in the lengthwise direction through contaminated tubing. Additionally, the sterilization head 310 can include a sensor system 320. In some embodiments a sensor system can be used to monitor UV radiation output. Wavelength ranges and intensity can be measured, with adjustments to power supplied to the LED UV emitters being made as necessary. In still other embodiments, the sensor system 320 can include detectors to monitor levels of particulates or microorganisms. In still other embodiments, the sensor system 320 can detect areas of relatively higher concentration of contaminates. In this case, the system can direct more radiation output from the LED emitters to areas of higher concentration of contaminates. The direction of radiation can be changed using optics 218 or using the beam steering ability of microLED arrays to direct emitted radiation.

The controller 340 can be used to set timing and duration of sterilization. In some embodiments, intensity can be dynamically changed in response to received sensor data from sensor system 320. In some embodiments, the controller 340 can provide visual status indication of detected sensor data or transmit that data to an external computing system such as smartphone.

Figure 4:
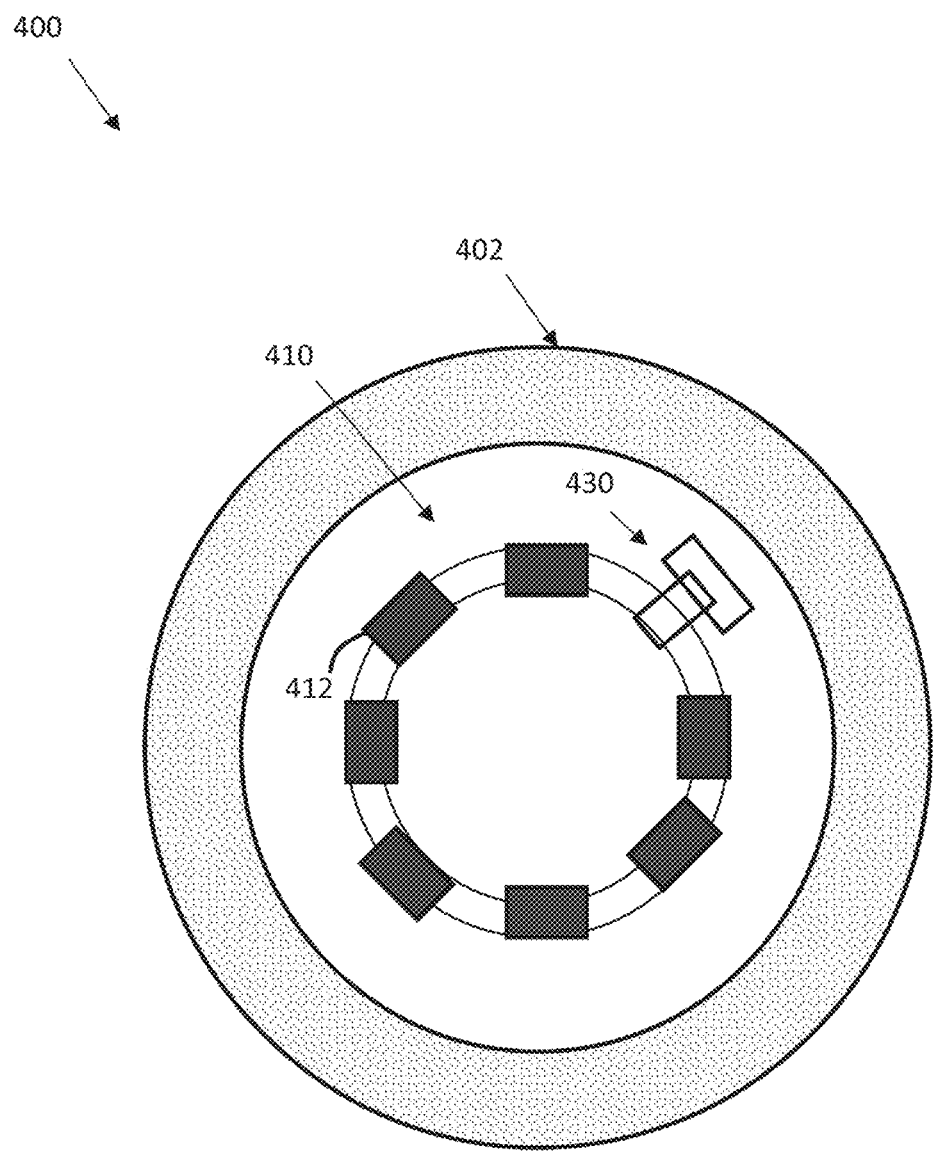
FIG. 4 illustrates an alternative UV sterilization system in cross section within a tube.

FIG. 4 illustrates an alternative UV sterilization system 400. FIG. 4 shows a cross section perpendicular to the long axis of a tube or catheter 402. Illustrated is a sterilization head 410 that includes UV LEDs 412 arrayed in a circle extending around the sterilization head 410. A flexible linearly extending connecter 430 is attached to hold the sterilization head 430. In FIG. 4, the linearly extending connector 430 is attached the sterilization head at a point offset from the central long axis of the sterilization head.

Figure 5A:
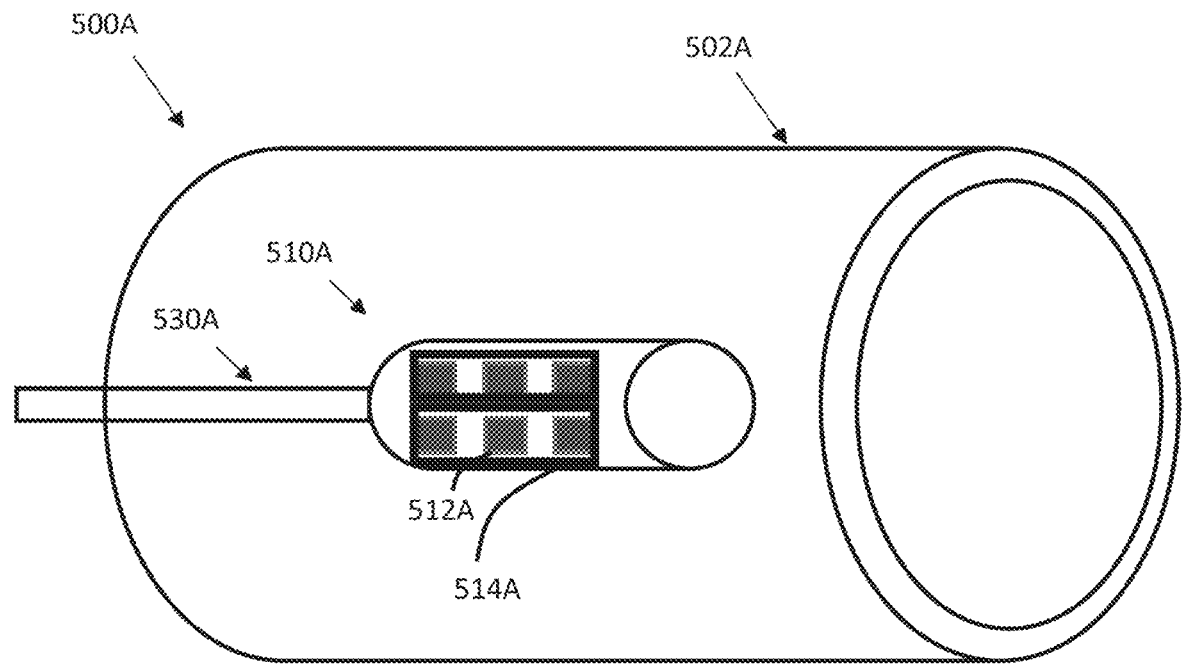
FIGS. 5A and 5B respectively illustrate a cartoon illustration and a picture of UV LEDs mounted on flexible strips.
Figure 5B:
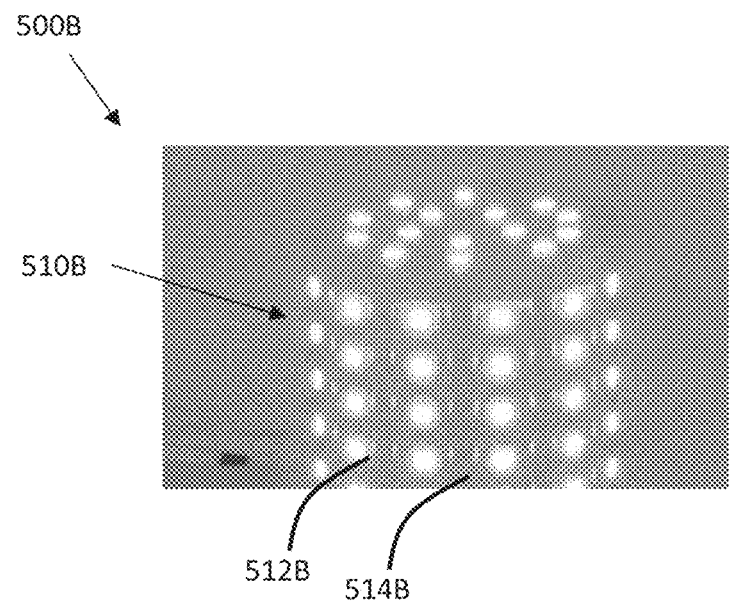

FIGS. 5A and 5B respectively illustrate a cartoon illustration 500A and a picture 500B of a sterilization head 510A (510B) with UV LEDs 512A (512B) mounted on flexible strips 514A (514B). The flexible strips 514A with the UV LEDs are arranged around a cylindrically shaped sterilization head. The use of flexible strips makes the whole sterilization head flexible allowing the sterilization head to navigate through sections of catheter tube 502A that are not straight.

Figure 6A:
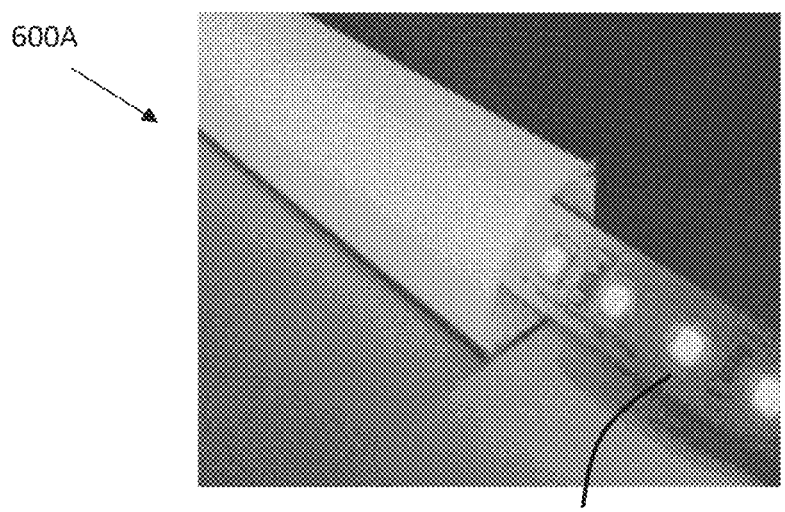
FIGS. 6A, 6B, and 6C respectively illustrate UV LEDs mounted on flexible strips, inserted in a housing, and mounted on a flexible connector.
Figure 6B:
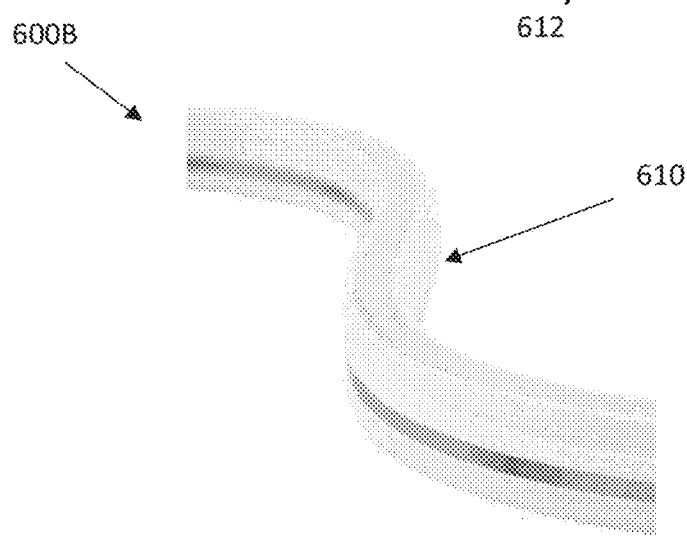
Figure 6C:
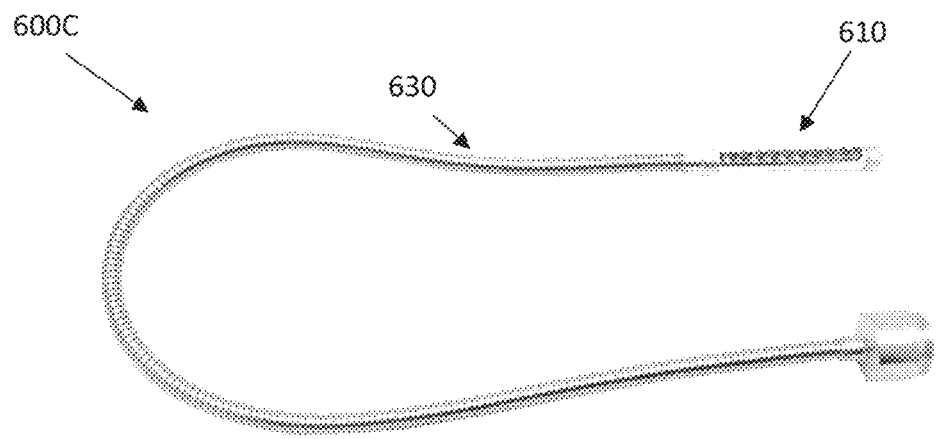

FIGS. 6A, 6B, and 6C respectively illustrate UV LEDs 612 mounted on flexible strips (image 600A), inserted in a housing of a sterilization head 610 (image 600B), and mounted on a flexible connector 630 attached to the sterilization head 610 (image 600C). FIG. 6A shows a UV LEDs 612 mounted on a flexible strip which can be inserted into a catheter tube to sterilize the catheter. The flexible strip can be rotated about the long axis of the catheter to sterilize the entire circumference of the inner sidewalls of the catheter. Alternately, light emitted from the LEDs 612 can be reflected off a reflective inner lining of the catheter to sterilize the circumference of the inner sidewalls of the catheter.

Figure 7:
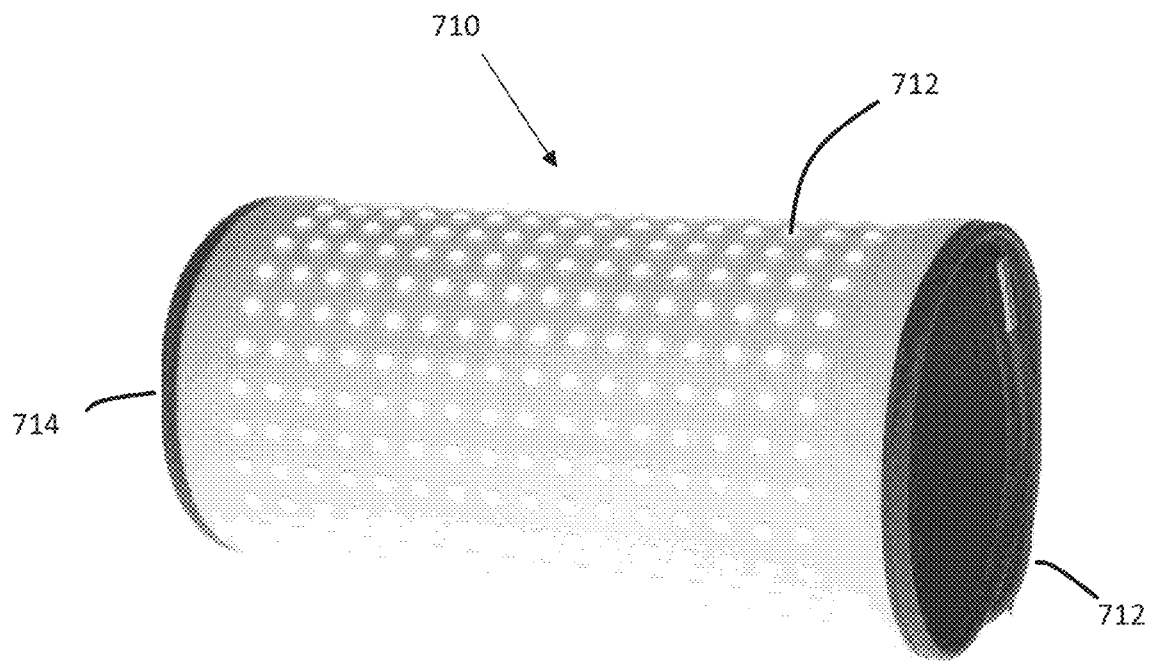
FIG. 7 is a picture of an example sterilization head with forward and rear UV blocking caps in position.

FIG. 7 is a picture of an example cylindrical sterilization head 710 supporting a wrap around array of UV LEDs 712.

Figure 8A:
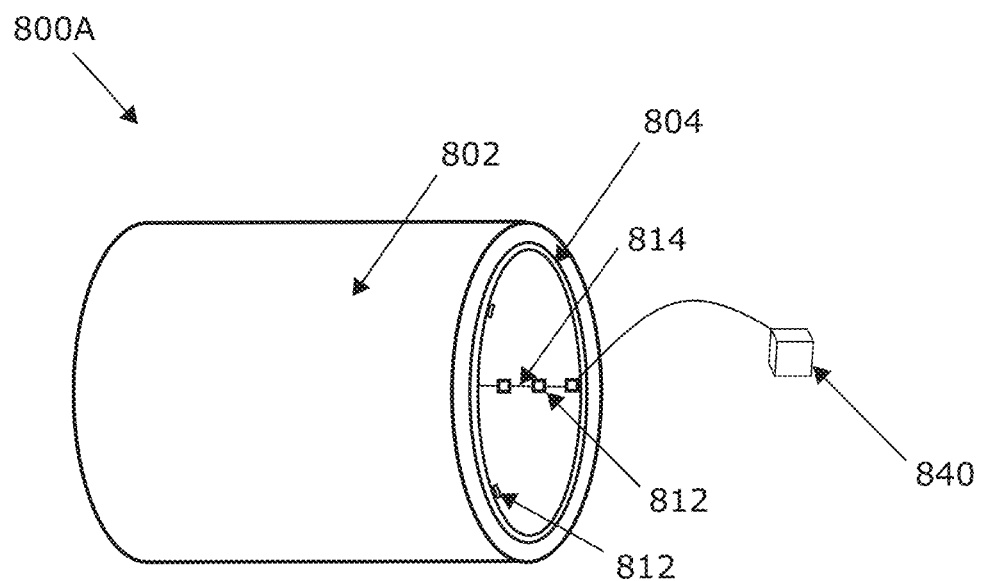
FIGS. 8A and 8B illustrate microLEDs mounted on the inner wall of a catheter.
Figure 8B:
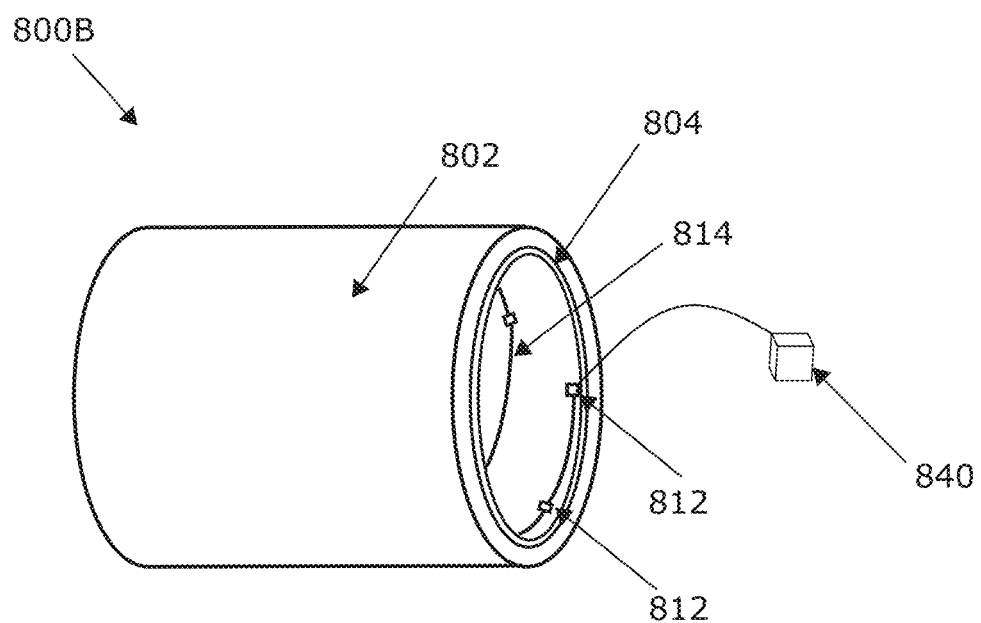

FIG. 8A illustrates an alternative embodiment of the UV sterilization system. The UV sterilization system 800A can sterilize catheter 802 using microLEDs 812 attached to the inner sidewalls of catheter 802. MicroLED 812 can also be an array of microLEDs, e.g., a microLED array. The microLEDs 812 are attached throughout the length of catheter 802 providing the ability to sterilize the catheter without any moving parts. The microLEDs 812 can also be arranged around a circumference of the catheter as shown in FIG. 8A. Micro LEDs because of their small size do not appreciably hinder the flexibility of the catheter. The catheter can have a light reflective or absorptive lining 804 to protect the patient from UV radiation emitted by the microLEDs 812. While FIGS. 8A and 8B illustrate the UV reflective lining 804 coating the inner wall of the catheter, UV reflective material can also be coated on the outer wall of the catheter. Using UV reflective lining has the advantage of reflecting the UV radiation emitted by the microLEDs 812 back into the lumen of the catheter thereby increase the effectiveness of the UV radiation at sterilizing contamination. The microLEDs 812 are connected by wiring 814 and connected to an external LED driver and/or controller 840. The microLEDs in FIG. 8A are arranged linearly along the long axis of catheter. Other arrangements of microLEDs within the catheter are possible. In the UV sterilization system 800B illustrated in FIG. 8B, the microLEDs 812 are arranged in a spiral along the inner sidewall of the catheter 802.

The UV sterilization systems of FIGS. 8A and 8B allow the catheter 802 to be sterilized while the catheter is still within the patient. This allows catheter 802 to be left within the patient for much longer periods of time decreasing the need to change the patient's catheter because of contamination risk. The catheter 802 can be programmed via an attached controller 840 to activate microLEDs 812 periodically to emit short duration bursts of UV-c radiation. The duration and intensity of the emitted radiation can be adjusted by programming the controller 840. For example, the catheter 802 can also be sterilized having microLED 812 emit a constant low dose (e.g., low intensity) radiation of longer wavelength UV. For example, the catheter 802 can be irradiated constantly with UV-a or violet-blue radiation of about 405 nanometers (nm). Studies have shown that 405 nm light has significant antimicrobial properties against a wide range of bacterial and fungal pathogens. The catheter 802 being constantly irradiated with 405 nm light would have a low risk of being contaminated with pathogens.

Having described the invention in detail, those skilled in the art will appreciate that, given the present disclosure, modifications may be made to the invention without departing from the spirit of the inventive concept described herein. Therefore, it is not intended that the scope of the invention be limited to the specific embodiments illustrated and described.

The invention claimed is:
1. A catheter sterilization system, comprising:
a linearly extending connector sized for insertion into the lumen of a catheter having inner sidewalls;
a sterilization head connected to the linearly extending connector, the sterilization head comprising:

at least one semiconductor LED emitter configured to emit UV light, the at least one semiconductor LED emitter comprising a light emission surface, the light emission surface arranged to be substantially parallel to a long axis of the catheter, and forward and rear UV blocking caps, the at least one semiconductor LED emitter positioned between the forward and rear UV blocking caps, the forward and rear UV blocking caps extending above the light emission surface of the at least one semiconductor LED emitter to at least partially block the UV light emitted by the at least one semiconductor LED emitter from traveling along the long axis of the catheter.

2. The catheter sterilization system of claim 1, wherein the linearly extending connector is flexible.

3. The catheter sterilization system of claim 1, wherein the linearly extending connector further provides an electrical connection to the at least one semiconductor LED emitter.

4. The catheter sterilization system of claim 1, further comprising a battery power module connected to the sterilization head.

5. The catheter sterilization system of claim 1, comprising at least one optic positioned to receive UV light from the at least one semiconductor LED emitter.

6. The catheter sterilization system of claim 1, wherein the sterilization head comprises a UV reflector attached to either the front or rear UV blocking cap.

7. A catheter sterilization system, comprising:
a catheter coated with a UV reflecting material,
a sterilization head sized for insertion into a lumen of the catheter, the sterilization head comprising at least one semiconductor LED emitter configured to emit UV light, the at least one semiconductor LED emitter comprising a light emission surface, the light emission surface arranged to be substantially parallel to a long axis of the catheter, and
a connector attached to the sterilization head, the connector allowing an operator to move the sterilization head through the lumen of the catheter in a direction parallel to the long axis of the catheter,
wherein the sterilization head comprises forward and rear UV blocking caps, the at least one semiconductor LED emitter positioned between the forward and rear UV blocking caps, the forward and rear UV blocking caps extending above the light emission surface of the at least one semiconductor LED emitter to at least partially block the UV light emitted by the at least one semiconductor LED emitter from traveling along the long axis of the catheter.

8. The catheter sterilization system of claim 7, wherein the connector is flexible.

9. The catheter sterilization system of claim 7, wherein the connector further provides an electrical connection to the at least one semiconductor LED emitter.

10. The catheter sterilization system of claim 7, further comprising a battery power module connected to the sterilization head.

* * * * *